United States Patent [19]

Schmelzer

[11] 4,419,627

[45] Dec. 6, 1983

[54] MEASURING THE MOISTURE CONTENT OF MATERIALS

[75] Inventor: Juergen F. Schmelzer, Bolton, Canada

[73] Assignee: Rothmans of Pall Mall Canada Limited, Toronto, Canada

[21] Appl. No.: 222,139

[22] Filed: Jan. 2, 1981

[30] Foreign Application Priority Data

Jan. 7, 1980 [GB] United Kingdom ................ 8000422

[51] Int. Cl.³ .................... H03K 5/00; G08B 21/00
[52] U.S. Cl. ........................................ 328/4; 307/308;
307/352; 328/151; 361/178
[58] Field of Search ................. 328/4, 151; 307/308,
307/352, 118; 340/602, 604; 200/61.04, 61.06;
361/178

[56] References Cited

U.S. PATENT DOCUMENTS

| | | | |
|---|---|---|---|
| 3,875,516 | 4/1975 | Thomas | 328/151 |
| 3,897,774 | 8/1975 | Burdick et al. | 328/151 |
| 3,999,134 | 12/1976 | Lorenzen | 328/4 |
| 4,053,874 | 10/1977 | Glaser | 361/178 |
| 4,161,660 | 7/1979 | Gallant | 328/4 |

Primary Examiner—Stanley D. Miller
Assistant Examiner—B. P. Davis
Attorney, Agent, or Firm—Sim & McBurney

[57] ABSTRACT

There is provided a method and apparatus for measuring the moisture content of materials, e.g., tobacco. In cases where the material flow is intermittent, the maximum moisture content of the last sample is indicated and held either for a predetermined time or until the moisture content of the next sample is determined.

4 Claims, 1 Drawing Figure

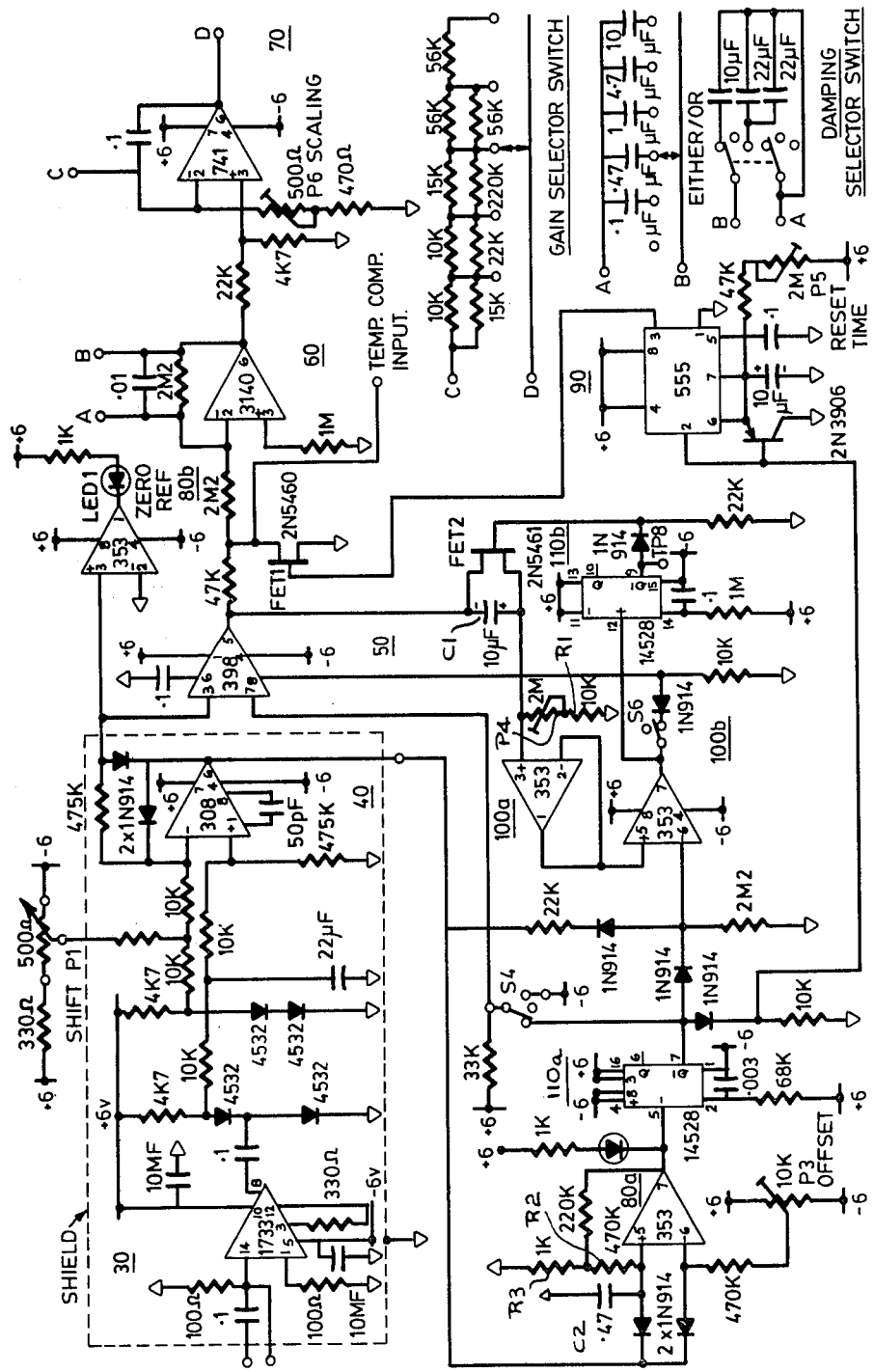

MEASURING THE MOISTURE CONTENT OF MATERIALS

This invention relates to the measurement of the moisture content of materials and is particularly useful for, although not limited to, measuring the moisture content of tobacco.

In U.S. Pat. No. 3,811,087 issued May 14, 1974, Juergen F. Schmelzer and assigned to Rothmans of Pall Mall Canada Limited a method and apparatus for measuring the moisture content of materials, e.g., tobacco, is disclosed. The system disclosed in the aforementioned patent is entirely satisfactory where there is a continuous flow of the material whose moisture content is being sensed by the probe disclosed in the patent. However, when the flow is intermittent, the system will indicate zero moisture content during periods of time when no material is passing over the probe, and the actual moisture content of the material at other times when it is passing over the probe, and the continuous fluctuation in readings may be puzzling to an operator and capable of being misinterpreted.

In accordance with an aspect of the present invention there is provided a method and apparatus for measuring the moisture content of materials wherein, during intermittent flow conditions, the maximum moisture content of the last sample passing the probe is determined and continues to be indicated until either a predetermined time has expired or a new sample passes over the probe.

Thus, according to one aspect of this invention there is provided apparatus for determining the moisture content of a material comprising means for deriving a D.C. signal having a magnitude that increases and decreases in direct proportion to increases and decreases respectively of the moisture content of the material; a comparator having first and second input terminals and an output terminal, said comparator providing an output signal at said output terminal thereof that changes from a first value to a second value different from said first value in response to said D.C. signal decreasing and that remains at said first value during application of said D.C. signal to said input terminals of said comparator and while said D.C. signal is level or increasing in magnitude; means for supplying said D.C. signal to said input terminals of said comparator; pulse producing means having an input terminal and an output terminal, said pulse producing means being responsive to said output signal of said comparator changing from said first value to said second value for producing an output pulse of predetermined pulse width at said output terminal of said pulse producing means; means for supplying said output signal of said comparator to said input terminal of said pulse producing means; a sample and hold network having first and second input terminals and an output terminal, said sample and hold network being adapted to derive at said output terminal thereof a moisture indicating output signal related to the signal applied to said first input terminal of said sample and hold network when said output pulse is applied to said second input terminal of said sample and hold network and to hold said output signal at said output terminal of said sample and hold network after said output pulse has terminated; means for supplying said output pulse to said second input terminal of said sample and hold network; means for supplying said D.C. signal to said first input terminal of said sample and hold network; timer means for producing an output signal after a predetermined time; means for resetting said timer means responsive to said output signal of said comparator changing from said first value to said second value; and means responsive to said output signal of said timer for inhibiting said sample and hold network from producing a moisture indicating output signal at least until another output pulse is produced by said pulse producing means.

This invention will become more apparent from the following detailed description, taken in conjunction with the appended drawing, which is a circuit diagram of one embodiment of apparatus for carrying out the instant invention.

Referring to the drawing, the apparatus embodying the instant invention shown therein includes a preamplifier 30, a rectifying and amplifying network 40, a sample and hold unit 50, a high impedance operational amplifier 60 providing damping action, an amplifier 70 providing output gain, a comparator 80a, a working range indicator unit 80b, a one shot multivibrator 110a, a timer 90 and a floating threshold system comprising operational amplifiers 100a and 100b and a one shot multivibrator 110b, all connected as shown in the drawing.

It should be noted that the numbers indicating the various components, e.g., 555 for timer 90, are standard manufacturers designations for the components.

In operation, an A.C. signal indicating the moisture content of a material by virtue of variations in the amplitude of the A.C. signal is derived and applied to pin 14 of preamplifier 30. The signal may be an R.F. signal and may be derived in any of a number of known ways. For example, it may be derived using the probe described in the aforementioned U.S. Patent, which is incorporated herein by reference.

Potentiometer P1 is used to select the desired operating range, this being achieved by changing the setting of potentiometer P1 to vary the bias voltage that is applied to one of the input terminals of the operational amplifier of network 40. The output signal of preamplifier 30 is applied to the other input terminal of the operational amplifier of network 40 and, provided that it is within the operating range preselected by potentiometer P1, is rectified and amplified by network 40 to provide a D.C. output signal at output pin 6 of the operational amplifier of network 40 that varies in amplitude responsive to the moisture content of the material being sampled, increasing in amplitude (becoming more negative) with increasing moisture content and vice versa. In this particular embodiment of the invention the moisture indicating output signal of network 40 is a negative D.C. voltage, but obviously a system could be designed where this signal was a positive D.C. voltage.

The D.C. output signal at pin 6 of the operational amplifier of network 40 is applied to pin 3 of sample and hold unit 50, to pin 3 of the operational amplifier of working range indicator unit 80b and via one diode each to the non-inverting (pin 5) and inverting (pin 6) inputs of the operational amplifier of comparator 80a.

The presence of a negative D.C. voltage at pin 6 of the operational amplifier of network 40 causes illumination of a light emitting diode LED1 connected to output pin 1 of the operational amplifier of working range indicator unit 80b, signifying that tobacco having a moisture content within the selected operating range of the system is being sensed.

With no input signal applied to pins 5 and 6 of the operational amplifier of comparator 80a, potentiometer P3 is adjusted so that the output voltage at pin 7 of this operational amplifier is positive. This is achieved by setting potentiometer P3 to apply a slightly negative voltage to the inverting input (pin 6) of the operational amplifier of comparator 80a, which thus appears as a positive voltage at pin 7 of this operational amplifier. This positive voltage is applied to pin 5 of one shot 110a, but since pin 5 is the negative edge sensitizer input terminal of the one shot, it is not triggered.

The negative D.C. voltage at pin 6 of the operational amplifier of network 40 is applied via diodes to pins 5 and 6 of the operational amplifier of comparator 80a. As long as the moisture indicating negative D.C. voltage continues to increase, it will be applied equally to both pins 5 and 6, and the additional bias provided via potentiometer P3 will keep the output of comparator 80a positive. A capacitor C2 connected to pin 5 of the operational amplifier of comparator 80a charges to the negative D.C. voltage applied to pin 5, and, as soon as the negative D.C. voltage at pin 6 of the operational amplifier of network 40 begins to decrease, signifying a drop in moisture content, the diode connected to pin 5 of the operational amplifier of comparator 80a becomes reverse biased. As a result of capacitor C2 commencing to discharge through resistors R2 and R3 producing a voltage at pin 5 of the operational amplifier of comparator 80a that is more negative than the negative D.C. voltage at pin 6 of the operational amplifier of network 40. The result is that a more negative voltage is applied to pin 5 than to pin 6 of the operational amplifier of comparator 80a, and since pin 5 in the non-inverting input, the output voltage of comparator 80a swings from positive to negative. The negative output voltage of comparator 80a triggers one shot 110a to produce a sampling pulse of predetermined length that is applied to pin 7 of sample and hold unit 50. Initiation of this pulse, which is a negative pulse, causes sample and hold unit 50 to open and sampling to occur. In other words, the negative D.C. voltage at pin 6 of the operational amplifier of network 40, which also is present at pin 3 of sample and hold unit 50, is supplied to putput pin 5 thereof. Sampling takes place for the duration of the sampling pulse. When the pulse terminates, the output at pin 5 of sample and hold unit 50 remains at the level obtained during sampling, which, assuming a short sampling pulse, is a level indicative of substantially the maximum moisture content sensed. In this manner the negative D.C. voltage at pin 6 of the operational amplifier of network 40 is sampled at substantially its peak negative value, and sampling is virtually independent of material frequency.

The high impedance operational amplifier 60 provides damping action and basically averages the D.C. output of sample and hold unit 50. Either of the damping networks shown at the right-hand side of the drawing may be connected to terminals A and B of the damping network.

Amplifier 70 amplifies the averaged D.C. signal to a desired level for recording, display and/or process control. The gain selector switch shown at the right-hand side of the drawing may be connected to terminals C and D of amplifier 70.

It should be noted in passing that the operational amplifier of comparator 80a has a positive feedback loop which insures a full positive or negative output depending upon input potentials.

In the event that there is now flow of material across the probe for some predetermined period of time, say, as a result of machine shutdown, it is undesirable for a moisture level to continue to be indicated. To this end the sampling pulse from one shot 110a is applied to pin 2 of timer 90 and resets the timer each time the state of the output of comparator 80a changes from positive to negative. In the event that timer 90 is not retriggered within a predetermined time, an output signal is produced at pin 3 thereof that turns on field effect transistor FET1 grounding the output of sample and hold unit 50. If desired the output at pin 3 of timer 90 also can be used to trigger a remote alarm.

In some cases, it may be desirable to provide a floating threshold. For example, consider the case where sampling of peak values only is desirable. In this set-up, the unit will, out of a group of "n" samples in a predetermined time, fetch only the higher values and lower its threshold level by means of an adjustable timing circuit if conditions change and new data is consistently of a smaller amplitude. When switch S6 is in the position shown in the drawing, a floating threshold is provided.

As may be seen from the drawing, pin 6 of operational amplifier 100b is connected to pin 7 of one shot 110a and to pin 6 of the operational amplifier of network 40. The nature of these connections is such that the voltage at pin 6 of operational amplifier 100b will not become negative until one shot 110a is triggered producing the aforementioned sampling pulse. At that time, and for the duration of the sampling pulse, the negative D.C. voltage at pin 6 of the operational amplifier of network 40 is applied to pin 6 of operational amplifier 100b. At this time operational amplifier 100b compares the new incoming negative D.C. voltage at pin 6 of the operational amplifier of network 40 with the previously sampled signal. In this respect, a timing network consisting of a capacitor C1, potentiometer P4 and resistor R1 is connected to pin 5 of sample and hold unit 50, and capacitor C1 will charge to the voltage at the output of sample and hold unit 50. Initially the magnitude of the voltage at pin 5 of operational amplifier 100b will be essentially the same as the negative output voltage of sample and hold unit 50. Assuming that the moisture content has decreased, the negative D.C. voltage applied to pin 6 of operational amplifier 100b when sampling occurs will be less than the negative D.C. voltage applied to pin 5 of operational amplifier 100b at this time, with the result that the output at pin 7 of operational amplifier 100b will be negative. The negative output of operational amplifier 100b is applied to pin 12 of one shot 110b but does not trigger the same, since this is the positive input of one shot 110b. The negative output of operational amplifier 100b also is applied to pin 8 of sample and hold unit 50 and prevents any sampling from occurring, since no sampling can occur until the voltage applied to pin 7 of sample and hold unit 50 is more negative than the voltage applied to pin 8 of sample and hold unit 50. However, capacitor C1 charges and, in due course the magnitude of the negative D.C. voltage applied to pin 5 of operational amplifier 100b will decrease below that of the negative D.C. voltage applied to pin 6 of operational amplifier 100b when sampling occurs. Under these circumstances the output voltage of operational amplifier 100b changes from negative to positive. The positive output voltage of operational amplifier 100b is supplied to pin 8 of sample and hold unit 50, permitting sampling to occur. It also is supplied to pin 12 of one shot 110b, triggering the same and producing a pulse which turns on a field effect transistor FET2 that causes capacitor C1 to discharge. Consequently, each time that sampling occurs, capacitor C1 is discharged and then begins to charge to the new output voltage at pin 5 of sample and hold unit 50, so that the threshold is continuously varied.

If a floating threshold is not desired, switch S6 can be moved to the other position shown in the figure.

While a preferred embodiment of this invention has been described herein, those skilled in the art will appreciate that changes and modifications can be made therein without departing from the spirit and scope of this invention as defined in the appended claims.

What is claimed is:

1. Apparatus for determining the moisture content of a material comprising means for deriving a D.C. signal having a magnitude that increases and decreases in direct proportion to increases and decreases respectively of the moisture content of the material; comparator having first and second input terminals and an output terminal, said comparator providing an output signal at said output terminal thereof that changes from a first value to a second value different from said first value in response to said D.C. signal decreasing and that remains at said first value during application of said D.C. signal to said input terminals of said comparator and while said D.C. signal is level or increasing in magnitude; means for supplying said D.C. signal to said input terminals of said comparator; pulse producing means having an input terminal and an output terminal, said pulse producing means being responsive to said output signal of said comparator changing from said first value to said second value for producing an output pulse of predetermined pulse width at said output terminal of said pulse producing means; means for supplying said output signal of said comparator to said input terminal of said pulse producing means; a sample and hold network having first and second input terminals and an output terminal, said sample and hold network being adapted to derive at said output terminal thereof a moisture indicating output signal related to the signal applied to the first input terminal of said sample and hold network when said output pulse is applied to said second input terminal of said sample and hold network and to hold said output signal at said output terminal of said sample and hold network after said output pulse has terminated; means for supplying said output pulse to said second input terminal of said sample and hold network; means for supplying said D.C. signal to said first input terminal of said sample and hold network; timer means for producing an output signal after a predetermined time; means for resetting said timer means responsive to said output signal of said comparator changing from said first value to said second value; and means responsive to said output signal of said timer for inhibiting said sample and hold network from producing a moisture indicating output signal at least until another output pulse is produced by said pulse producing means.

2. Apparatus according to claim 1 wherein said pulse producing means is a one shot multivibrator.

3. Apparatus according to claim 1 wherein said means for inhibiting said sample and hold network comprises switching means for connecting said output terminal of said sample and hold network to ground.

4. Apparatus according to claim 1 including means for deriving a threshold voltage that increases and decreases with increases and decreases respectively in said D.C. signal; and means for inhibiting said sample and hold network from producing a moisture indicating output signal related to said D.C. signal applied to said first input terminal of said sample and hold network when said D.C. signal is of a magnitude that is less than the magnitude of said threshold voltage.

* * * * *